United States Patent [19]
Luther

[11] Patent Number: 5,522,807
[45] Date of Patent: Jun. 4, 1996

[54] DUAL LUMEN INFUSION/ASPIRATION CATHETER

[75] Inventor: Ronald B. Luther, Newport Beach, Calif.

[73] Assignee: Luther Medical Products, Inc., Tustin, Calif.

[21] Appl. No.: 302,522

[22] Filed: Sep. 7, 1994

[51] Int. Cl.$^6$ ...................................................... A61M 5/00
[52] U.S. Cl. .......................... 604/264; 604/280; 604/256
[58] Field of Search ...................... 128/656, 657, 128/658; 137/843, 845; 604/31, 52, 53, 101, 170, 96, 264, 280, 247, 118, 246, 256, 266; 606/194

[56] References Cited

U.S. PATENT DOCUMENTS

| | | |
|---|---|---|
| 561,059 | 5/1896 | Mitchell . |
| 3,225,762 | 12/1965 | Guttman . |
| 3,352,306 | 11/1967 | Hirsch . |
| 3,463,152 | 8/1969 | Sorenson . |
| 3,630,195 | 12/1971 | Santomieri . |
| 3,834,380 | 9/1974 | Boyd . |
| 4,194,504 | 3/1980 | Harms et al. . |
| 4,249,541 | 2/1981 | Pratt . |
| 4,327,722 | 5/1982 | Groshong et al. . |
| 4,353,369 | 10/1982 | Muetterties . |
| 4,392,856 | 7/1983 | Lichtenstein . |
| 4,431,426 | 2/1984 | Groshong et al. . |
| 4,439,583 | 3/1984 | Gould et al. . |
| 4,525,157 | 6/1985 | Vaillancourt . |
| 4,529,399 | 7/1985 | Groshong et al. . |
| 4,549,879 | 10/1985 | Groshong et al. . |
| 4,559,046 | 12/1985 | Groshong et al. . |
| 4,588,398 | 5/1986 | Daugherty et al. . |
| 4,627,841 | 12/1986 | Dorr . |
| 4,668,225 | 5/1987 | Russo et al. . |
| 4,671,795 | 6/1987 | Mulchin . |
| 4,671,796 | 6/1987 | Groshong et al. . |
| 4,690,675 | 9/1987 | Katz . |
| 4,701,166 | 10/1987 | Groshong et al. . |
| 4,728,322 | 3/1988 | Walker et al. . |
| 4,753,640 | 6/1988 | Nichols et al. ........................ 604/247 |
| 4,770,655 | 9/1988 | Haber et al. . |
| 4,772,264 | 9/1988 | Cragg . |
| 4,772,276 | 9/1888 | Wiita et al. . |
| 4,773,901 | 9/1988 | Norton . |
| 4,798,597 | 1/1989 | Vaillancourt . |
| 4,828,549 | 5/1989 | Kvalo . |
| 4,846,799 | 7/1989 | Tanaka et al. . |
| 4,846,812 | 7/1989 | Walker et al. . |
| 4,863,432 | 9/1989 | Kvalo . |
| 4,887,998 | 12/1989 | Martin et al. . |
| 4,895,564 | 1/1990 | Farrell . |
| 4,898,591 | 2/1990 | Jang et al. . |
| 4,911,691 | 3/1990 | Aniuk et al. . |
| 4,917,671 | 4/1990 | Chang . |
| 4,927,415 | 5/1990 | Brodsky . |
| 4,944,728 | 7/1990 | Carrell et al. . |
| 4,950,252 | 8/1990 | Luther et al. . |
| 4,955,863 | 9/1990 | Walker et al. . |
| 4,973,319 | 11/1990 | Melsky .................................. 604/247 |

(List continued on next page.)

*Primary Examiner*—Corrine M. Maglione
*Assistant Examiner*—N. Kent Gring
*Attorney, Agent, or Firm*—Stetina Brunda & Buyan

[57] ABSTRACT

A catheter having an elongate body has a first lumen extending therethrough. A concave wall is formed in the body proximate the distal end thereof such that the concave wall is a wall of the first lumen. A first slit is formed in the concave wall. The first slit opens in response to decreased fluid pressure within the lumen so as to facilitate aspiration via the first lumen. Optionally, a first convex wall is formed in the body such that the first convex wall is a wall of the first lumen. A second slit is formed in the first convex wall. The second slit opens in response to increased fluid pressure within the first lumen so as to facilitate infusion via the first lumen. Optionally, a second lumen extends through a substantial portion of the body. A second convex wall is formed in the body proximate the distal end thereof such that the second convex wall is a wall of the second lumen. A third slit is formed in the second convex wall. The third slit opens in response to increased fluid pressure within the second lumen so as to facilitate infusion via the second lumen.

5 Claims, 1 Drawing Sheet

U.S. PATENT DOCUMENTS

| | | |
|---|---|---|
| 4,976,704 | 12/1990 | McLees . |
| 4,986,814 | 1/1991 | Burney et al. . |
| 4,994,046 | 2/1991 | Wesson et al. . |
| 4,995,863 | 2/1991 | Nichols et al. .......................... 604/247 |
| 4,998,919 | 3/1991 | Schnepp-Pesch . |
| 5,002,533 | 3/1991 | Jullien . |
| 5,026,353 | 6/1991 | Bartman . |
| 5,030,210 | 7/1991 | Alchas .................................... 604/247 |
| 5,037,402 | 8/1991 | Bartman . |
| 5,112,312 | 5/1992 | Luther . |
| 5,120,317 | 6/1992 | Luther . |
| 5,135,502 | 8/1992 | Koenig, Jr. . |
| 5,147,332 | 9/1992 | Moorehead . |
| 5,160,325 | 11/1992 | Nichols et al. .......................... 604/247 |
| 5,205,829 | 4/1993 | Lituchy . |
| 5,224,938 | 7/1993 | Fenton, Jr. .............................. 604/247 |
| 5,261,885 | 11/1993 | Lui ......................................... 604/247 |
| 5,273,540 | 12/1993 | Luther et al. . |
| 5,304,155 | 4/1994 | Lui ........................................... 604/31 |

DUAL LUMEN INFUSION/ASPIRATION CATHETER

FIELD OF THE INVENTION

The present invention relates generally to catheters and more particularly to a dual lumen infusion/aspiration catheter wherein a first lumen has both an infusion slit valve and an aspiration slit valve while a second lumen has only an infusion slit valve. The infusion slit valve of the second lumen is positioned so as to facilitate cleaning of the exterior surface of the aspiration slit valve of the first lumen.

BACKGROUND OF THE INVENTION

Catheters for drug infusion and fluid aspiration are well known. Such catheters are frequently positioned within the vascular system of a patient for long term therapy, e.g., the administration of saline, nutrients, medication, etc.

However, one problem commonly associated with the use of catheters, particularly when left in position for an extended length of time, is that clotting or thrombosis commonly occurs around the distal opening of the catheter lumen. Although this effect is most pronounced when such catheters are used for aspiration, it is not unknown for thrombosis to occur at the distal opening of a catheter utilized for infusion due to the effects of retrograde blood flow into the catheter. Thus, it is possible for a thrombosis to substantially or even completely obstruct fluid flow through the catheter over an extended period of time, thereby posing a potentially life threatening risk for the patient.

Further, it is also possible for a clot or thrombus to form at the distal end of a catheter and then break loose from the catheter and flow through the vascular system to a point where the thrombus comes to rest within a portion of the vascular system wherein the diameter of the vessel is less than the diameter of the thrombus. As such, it will be appreciated that the thrombus necessarily impedes further flow of blood through the vessel. Such breaking loose of thrombus from the catheter is commonly caused by flushing of the catheter in an attempt to mitigate the effects of thrombus upon fluid flow through the catheter lumen.

As will be appreciated, if a thrombus breaks loose from the catheter and subsequently obstructs a blood vessel of a critical organ such as the brain, heart, or lung, the results of such blockage may potentially be very serious, possibly even fatal. Stroke, heart attack, and pulmonary embolism have been known to result from such blockage.

In an attempt to prevent the retrograde fluid flow which causes such thrombosis, contemporary practice is to utilize a closed end catheter having a single, longitudinally extending, slit valve disposed near the distal end thereof. The slit tends to close when fluid is not flowing therethrough, thereby mitigating retrograde fluid flow.

Such slit valves, when formed in the convex circular wall of a catheter, are subject to a keystone effect, wherein the slit easily facilitates infusion by spreading open when the fluid pressure within the catheter is increased, i.e., greater than that outside thereof, but does not readily facilitate aspiration when the fluid pressure within the catheter is reduced, i.e., lower than that outside thereof. More particularly, when the fluid pressure inside of the catheter is slightly lower than that outside thereof, the two sides of the slit valve tend to be urged even tighter together. A substantially lower pressure is thus required within the catheter as compared to that outside thereof in order to force the two sides of the slit valve to bend sufficiently inward so as to effect substantial opening of the slit. The slit valve therefore requires a substantially greater pressure differential to effect aspiration than it does to effect infusion. Thus, as will be appreciated by those skilled in the art, a slit valve formed in the convex surface of a circular catheter wall is much more efficient for effecting infusion than for effecting aspiration.

In an attempt to overcome the keystone effect in contemporary catheter construction, the catheter wall within which the slit valve is formed may be weakened, by treating with dimethylsiloxane, for example. Optionally, the slit valve may be formed upon a planar surface within a recess formed at the distal end of the catheter. By forming the slit upon a planar surface, a two-way slit valve is provided. Both infusion and aspiration may be performed via such a two-way slit valve. Thus, when the slit is formed upon a planar portion of the catheter, fluid flows therethrough in either direction with equal ease. Furthermore, there is no substantial difference in the pressure differential required for infusion and aspiration. One example of a catheter utilizing a slit formed upon a planar surface within a recess is disclosed in U.S. Pat. No. 5,261,885 issued to Lui on Nov. 16, 1993 and entitled VALVED CATHETER.

Additionally, slit valves may be formed without chemically weakening the walls of the catheter by utilizing lumen geometry which inherently provides weakened portions of the catheter wall which act as hinges. The hinges facilitate opening and closing of the slit valves. One example of a catheter utilizing such construction is disclosed in U.S. Pat. No. 4,753,640 issued to Nichols et al. on Jun. 28, 1988 and entitled CATHETERS AND METHODS.

However, one disadvantage of such contemporary slit valve catheters is that they tend to be inherently complex in construction, thus undesirably increasing the cost thereof. As such, although such construction does overcome the problems associated with the keystone effect, it does so at considerable cost. Additionally, such slit valve catheters are not completely immune to the effects of thrombosis, particularly when utilized for extended periods of time.

In view of the shortcomings of the prior art, it is desirable to provide a catheter which may be utilized for either infusion or aspiration without the performance or cost thereof being adversely affected by the keystone effect, and which is less prone to the undesirable effects of thrombosis than contemporary catheters.

SUMMARY OF THE INVENTION

The present invention specifically addresses and alleviates the above-mentioned deficiencies associated with the prior art. It does so by taking advantage of the keystone effect, rather than by attempting to eliminate the same. Thus, construction according to the present invention facilitates the formation of slit valves in the circular wall of a catheter, thereby substantially reducing the cost thereof. Although the wall of the catheter is, for one of the slit valves, modified somewhat so as to take advantage of the keystone effect in a manner which facilitates aspiration, such modification is comparatively simple as compared to contemporary catheter construction for similarly facilitating aspiration via a slit valve.

More particularly, the present invention comprises a dual lumen infusion/aspiration catheter comprising an elongate body having proximal and distal ends and a first lumen extending through a substantial portion of the body. A non-convex wall, e.g., either concave or planar, is formed in the body, preferably proximate the distal end thereof and forms a wall of the first lumen. A first slit is formed in the non-convex wall. The first slit opens in response to decreased fluid pressure within the lumen so as to facilitate aspiration via the first lumen.

A first convex wall is also formed in the body, such that the first convex wall is also a wall of the first lumen. A second slit is formed in the first convex wall such that the second slit opens in response to increased fluid pressure within the first lumen so as to facilitate infusion via the first lumen.

A second lumen preferably extends through a substantial portion of the body, preferably alongside of the first lumen. A second convex wall is formed in the body, preferably proximate the distal end thereof such that the second convex wall is a wall of the second lumen. A third slit is formed in the second convex wall such that the third slit opens in response to increased fluid pressure within the second lumen so as to facilitate infusion via the second lumen.

The first slit is preferably formed distal of the third slit such that the third slit may be utilized to flush a fluid over the first slit so as to prevent the formation of thrombus proximate the first slit.

Thus, the keystone effect readily allows the two sides of the first slit to bend inward in response to decreased pressure within the first lumen so as to facilitate aspiration via the first lumen, while causing the two sides of the first slit to close in response to increased pressure within the first lumen. The keystone effect allows the two sides of the second slit to bend outward in response to increased pressure within the first lumen so as to facilitate infusion therethrough while causing the two sides of the first slit to bend outward and thereby close the first slit in response to the increased pressure within the first lumen. The two sides of the third slit bend outward in response to increased pressure within the second lumen so as to facilitate infusion via the third slit.

Thus, according to the present invention, a low cost, easy to fabricate catheter is provided which takes advantage of the keystone effect to facilitate both infusion and aspiration and which also mitigates the likelihood of the formation of thrombus at the distal end of the catheter.

These, as well as other advantages of the present invention will be more apparent from the following description and drawings. It is understood that changes in the structure shown and described may be made within the scope of the claims without departing from the spirit of the invention.

DETAILED DESCRIPTION OF THE PREFERRED EMBODIMENT

The detailed description set forth below in connection with the appended drawings is intended as a description of the presently preferred embodiments of the invention, and is not intended to represent the only forms in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
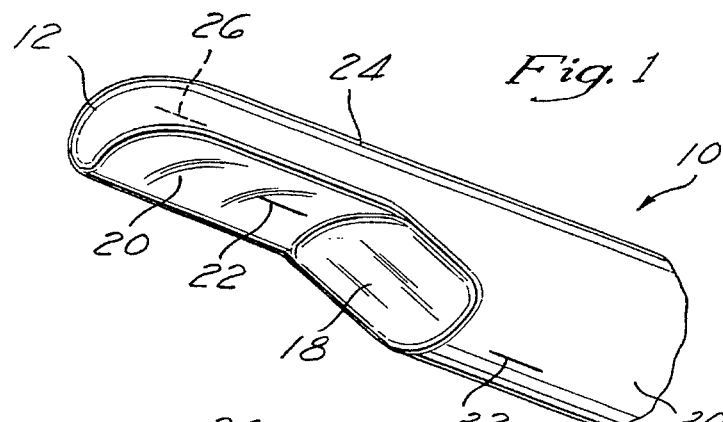
FIG. 1 is a perspective view of the distal end of a first embodiment of the dual lumen infusion/aspiration catheter of the present invention.
Figure 2:
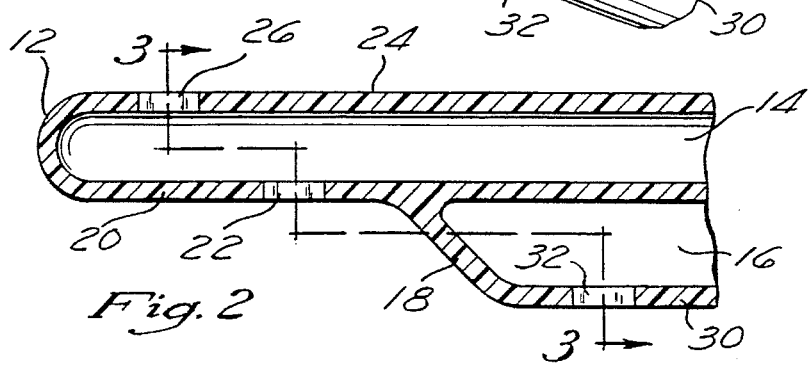
FIG. 2 is a cross-sectional side view of the distal end of the dual lumen infusion/aspiration catheter of FIG. 1.
Figure 3:
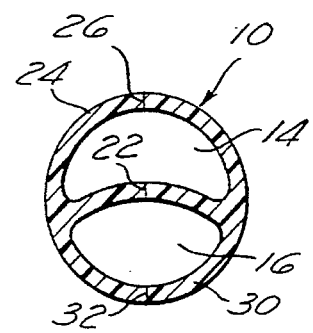
FIG. 3 is a cross-sectional end view taken along lines 3 of FIG. 2.

The dual lumen infusion/aspiration catheter of the present invention is illustrated in FIGS. 1–8d which depict five presently preferred embodiments of the invention. Referring now to FIGS. 1–3, the first embodiment of the dual lumen infusion/aspiration catheter is comprised generally of an elongate catheter body 10 having a closed distal end 12. A first lumen 14 extends through the catheter body 10 to the distal end 12 thereof. A second lumen 16 similarly extends alongside of the first lumen 14, but preferably terminates just short of the distal end 12. The second lumen 16 preferably terminates with a ramped or sloped surface 18 so as to facilitate easy introduction and manipulation thereof within a patient's vascular system. A non-convex wall, preferably a concave wall 20 is formed in the catheter body 10 proximate the distal end 12 thereof such that the concave wall 20 is a wall of the first lumen 14. Alternatively, the non-convex wall may comprise a planar wall. Those skilled in the art will appreciate that various non-convex configurations are likewise suitable. A first slit 22 is formed in the concave wall 20 so as to form a first slit valve. The first slit 22 opens in response to decreased fluid pressure within the first lumen 14 so as to facilitate aspiration via the first lumen 14.

A first convex wall 24 is similarly formed in the catheter body 10 proximate the distal end 12 thereof such that the first convex wall 24 is also a wall of the first lumen 14. A second slit 26 is formed in the first convex wall 24 so as to form a second slit valve. The second slit 26 opens in response to increased fluid pressure within the first lumen 14 so as to facilitate infusion via the first lumen 14.

A second lumen 16 is formed parallel the first lumen 14 and preferably shares a common wall 28 therewith. A second convex wall 30 is formed in the catheter body 10 proximate the sloped surface 18 of the second lumen 16. A third slit 32 is formed in the second convex wall 30 so as to form a third slit valve. The third slit 32 opens in response to increased fluid pressure within the second lumen 16, so as to facilitate infusion via the second lumen 16.

The first slit 22 is preferably formed distal of the third slit 32 such that the third slit 32 may be utilized to flush fluid over the first slit 22 by providing infusion via the third slit 32, so as to prevent the formation of thrombus proximate the first slit 22. Thus, as thrombus begins to form proximate the first slit 22, as is common during the aspiration process, aspiration can periodically be halted and fluid infused via the second slit 32 so as to wash over the first slit 22, thereby mitigating the formation of thrombus proximate the first slit 22.

Having thus described the structure of the first embodiment of the dual lumen infusion/aspiration catheter of the present invention, it may be beneficial to discuss the use thereof. Referring now to FIGS. 4–7, the first 22, second 26, and third 32 slits are shown in various positions, i.e., open or closed, so as to illustrate different operational configurations of the first embodiment of the present invention.

Figure 4:
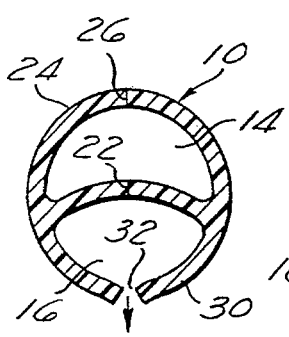
FIG. 4 is the cross-sectional end view of FIG. 3 showing infusion via the second lumen thereof.

With particular reference to FIG. 4, infusion via the second lumen 16 is illustrated. During infusion via the second lumen 16, increased fluid pressure within the second lumen 16 causes the two sides of the third slit 32 to spread apart, thereby opening the third slit 32 and allowing fluid to infuse from the second lumen 16 through the second slit 32.

Figure 5:
FIG. 5 is the cross-sectional end view of FIG. 3 showing aspiration via the first lumen thereof.

With particular reference to FIG. 5, aspiration via the first lumen 14 as illustrated. During aspiration, the fluid pressure within the first lumen 14 is decreased such that the two sides of the first slit 22 spread apart, thereby opening the first slit 22 so as to facilitate fluid flow into the first lumen 14. The keystone effect causes the two sides of the second slit 26 to remain tightly abutted against one another, thereby closing the second slit 26 and preventing fluid flow therethrough.

Figure 6:
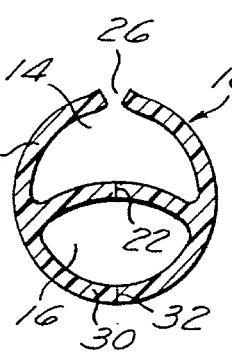
FIG. 6 is the cross-sectional end view of FIG. 3 showing infusion via the first lumen thereof.

With particular reference to FIG. 6, infusion via the first lumen 14 is illustrated. During infusion, increased fluid pressure within the first lumen 14 causes the two sides of the second slit 26 to spread apart and open the second slit 26 so as to cause fluid to flow from the first lumen 14 through the second slit 26. The keystone effect causes the two sides of the first slit 22 to abut one another, thereby closing the first slit 22 and preventing fluid flow therethrough.

Figure 7:
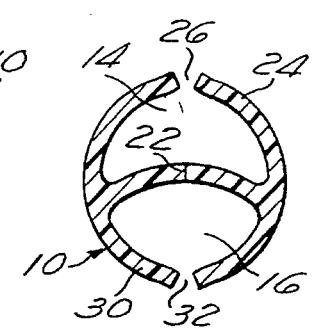
FIG. 7 is the cross-sectional end view of FIG. 3 showing simultaneous infusion via the first and second lumens.

With particular reference to FIG. 7, simultaneous infusion via the first 14 and second 16 lumens is illustrated. During simultaneous infusion, increased pressure within the first lumen 14 causes the two sides of the second slit 26 to spread apart and open the second slit 26 such that fluid flows from the first lumen through the second slit 26. Simultaneously, increased pressure within the second lumen 16 causes the two sides of the third slit 32 to spread apart and open the third slit 32 such that fluid flows from the second lumen 26 through the third slit 32. The keystone effect causes the two sides of the first slit 22 to abut one another, thereby closing the first slit 22.

Thus, the keystone effect is utilized so as to facilitate controlled infusion and aspiration through the desired slits of the dual lumen infusion/aspiration catheter of the present invention. The use of such slits minimizes flow when neither infusion nor aspiration is taking place, thereby mitigating the formation of thrombosis. Flow is minimized since the slits tend to close when no pressure differential is applied thereacross.

As mentioned above, the third slit may be utilized to effect infusion so as to wash the outer surface of the first slit 22, thereby further mitigating the formation of thrombosis proximate the first slit 22.

Figure 8A:
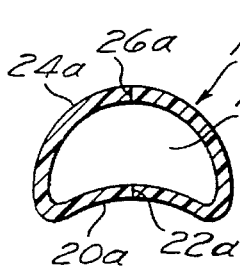
FIG. 8a is a cross-sectional end view analogous to that of FIG. 3 for a second embodiment of the present invention comprising a single lumen catheter capable of both infusion and aspiration and having a cross-sectional configuration similar to that of the first lumen of the dual lumen catheter of FIG. 1.

Referring now to FIG. 8a, in a second embodiment of the present invention a single lumen 14a is formed within a catheter body 10a having a concave surface 20a within which is formed a first slit 22a and also having a convex surface 24a within which is formed a second slit 26a. Thus, the elongate body, preferably proximate the distal end thereof, is shaped similar to that portion of the elongate body formed about the first lumen of the first embodiment of the present invention.

Figure 8B:
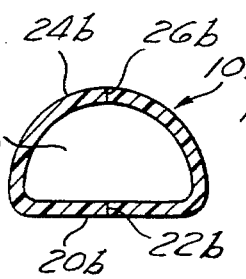
FIG. 8b is a cross-sectional end view analogous to that of FIG. 3 for a third embodiment of the present invention comprising a single lumen catheter capable of both infusion and aspiration and having a cross-sectional configuration similar to the letter D.

Referring now to FIG. 8b, in a third embodiment of the present invention a single lumen 14b is formed within a catheter body 10b having a planar surface 20b within which a first slit 22b is formed and also having a convex surface 24b within which a second slit 26b is formed. Thus, the elongate body, preferably proximate the distal end thereof, is shaped substantially like the letter D.

Figure 8C:
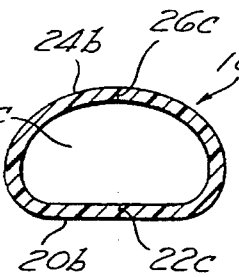
FIG. 8c is a cross-sectional end view analogous to that of FIG. 3 for a fourth embodiment of the present invention comprising a single lumen catheter capable of both infusion and aspiration and having a generally oval cross-sectional configuration.

Referring now to FIG. 8c, in a fourth embodiment of the present invention a single lumen 14c is formed within a catheter body 10c having a planar surface 20c within which a first slit 22c is formed and also having a convex surface 24c within which a second slit 26c is formed. Thus, the catheter body 10c, preferably proximate the distal end of the catheter body 10c, is substantially oval in shape, and has one generally flat side.

Figure 8D:
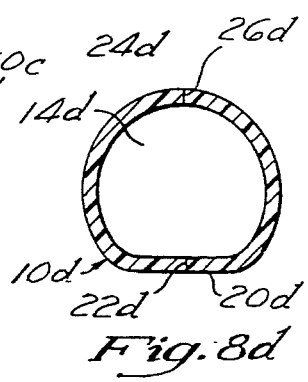
FIG. 8d is a cross-sectional end view analogous to that of FIG. 3 for a fifth embodiment of the present invention comprising a single lumen catheter capable of both infusion and aspiration and having a generally circular cross-sectional configuration wherein the first slit is formed upon a generally flat wall thereof.

Referring now to FIG. 8d, in a fifth embodiment of the present invention a single lumen 14d is formed within a catheter body 10d having a planar surface 20d within which a first slit 22d is formed and also having a convex surface 24d within which a second slit 26d is formed. Thus, the catheter body 10d, preferably proximate the distal end thereof, is substantially circular in shape, and has a flat side formed thereon.

The second, third, fourth, and fifth embodiments of the present invention are utilized in a manner analogous to that of the first embodiment thereof, with the exception that no second lumen is provided such that all infusion and/or aspiration takes place through the single lumen 14a–d. In each embodiment, the keystone effect is utilized so as to cause aspiration to occur via the first slit 22a–d and infusion to occur via the second slit 26a–d.

The key feature of the non-convex wall is that it not be convex in configuration so as to take proper advantage of the keystone effect in causing the first slit 22 to open in response to decreased fluid pressure within the first lumen 14a–d and preferably also to close in response to increased pressure within the first lumen 14a–d.

It is understood that the exemplary dual lumen infusion/aspiration catheter described herein and shown in the drawings represents only a presently preferred embodiment of the invention. Indeed, various modifications and additions may be made to such embodiment without departing from the spirit and scope of the invention. For example, various cross-sectional configurations other than those illustrated in FIGS. 3 and 8a–8d are contemplated. Also, the slits may alternatively be disposed at various positions either radially or along the length of the catheter body and need not even be positioned proximate the distal end thereof as discussed and illustrated. Thus, these and other modifications and additions may be obvious to those skilled in the art and may be implemented to adapt the present invention for use in a variety of different applications.

What is claimed is:

1. A catheter comprising:
   a) an elongate body having proximal and distal ends;
   b) a first lumen extending through a substantial portion of said body;
   c) a concave wall formed in said body, said concave wall being a wall of said first lumen;
   d) a first slit formed in said concave wall; and
   e) wherein said first slit opens in response to decreased fluid pressure within said first lumen so as to facilitate aspiration via said first lumen and closes in response to increased fluid pressure so as to prevent undesirable infusion via said first lumen.

2. The catheter as recited in claim 1 further comprising:
   a) a first convex wall formed in said body, said first convex wall being a wall of said first lumen;
   b) a second slit formed in said first convex wall; and
   c) wherein said second slit opens and said first slit closes in response to increased fluid pressure with said first lumen so as to facilitate infusion via said first lumen.

3. The catheter as recited in claim 1 further comprising:
   a) a second lumen extending through a substantial portion of said body;
   b) a second convex wall formed in said body, said second convex wall being a wall of said second lumen;
   c) a third slit formed in said second convex wall; and
   d) wherein said third slit opens in response to increased fluid pressure within said second lumen so as to facilitate infusion via said second lumen.

4. The catheter as recited in claim 3 wherein said first slit is formed distal of said third slit.

5. The catheter as recited in claim 3 wherein said concave wall, said first convex wall, and said second convex wall are formed proximate the distal end of said body.

* * * * *